United States Patent [19]

Sugiyama et al.

[11] Patent Number: 4,773,761
[45] Date of Patent: Sep. 27, 1988

[54] PHOTOELECTRIC COLORIMETER

[75] Inventors: Masami Sugiyama, Toyonaka; Yoshihiro Tasaka, Nishinomiya, both of Japan

[73] Assignee: Minolta Camera Kabushiki Kaisha, Osaka, Japan

[21] Appl. No.: 942,446

[22] Filed: Dec. 16, 1986

[30] Foreign Application Priority Data

Dec. 16, 1985 [JP] Japan ................................. 60-283957
Dec. 9, 1986 [JP] Japan ................................. 61-293689

[51] Int. Cl.4 ............................................ G01N 21/25
[52] U.S. Cl. ..................................... 356/405; 356/416; 364/571.04
[58] Field of Search ............... 356/405, 408, 425, 416; 364/526, 571

[56] References Cited

U.S. PATENT DOCUMENTS

| | | | |
|---|---|---|---|
| 4,055,813 | 10/1977 | French ................ | 330/103 |
| 4,125,329 | 11/1978 | French et al. ........ | 356/405 |
| 4,165,180 | 8/1979 | Failes ................. | 364/526 X |
| 4,350,441 | 9/1982 | Wicnienski ........... | 356/408 X |
| 4,654,794 | 3/1987 | O'Brien ............... | 356/405 X |

FOREIGN PATENT DOCUMENTS 0169726  9/1985  Japan .................................. 364/526

Primary Examiner—Eugene R. LaRoche
Assistant Examiner—Seung Ham
Attorney, Agent, or Firm—Price, Gess & Ubell

[57] ABSTRACT

A photoelectric colorimeter which comprises a photoelectric conversion section including an optical filter to analyze light coming from a test piece and a reference calibrating sample into primary color elements, and a photosensor to convert each of said primary color elements into an electric signal; and a data processing section including a calibration constant calculating device for calculating a calibration constant for each of a plurality of reference calibrating samples on the basis of a calibration point of each of the reference calibrating samples and an information inputted from said photoelectric conversion section, a chromaticity point calculation device for calculating a chromaticity point of the test piece and that of each reference calibrating sample, a memory device for memorizing the calibration constant and calibration point of each of the reference calibrating samples, a device for estimating a new calibration constant suitable for the chromaticity point of the test piece between the respective calibration constants of the reference calibrating samples through the interpolation using a positional relation between the chromaticity point of the calibration point and that of the test piece as a parameter, and a correction device for correcting measured value of the test piece by the new calibration constant.

17 Claims, 10 Drawing Sheets

PHOTOELECTRIC COLORIMETER

BACKGROUND OF THE INVENTION

The present invention relates to a tristimulus value type photoelectric colorimeter with spectral sensitivity correcting function.

Conventionally, the photoelectric colorimeter (of tristimulus value type) is given a spectral sensitivity close to an isochromatic function $[\bar{x}(\gamma), \bar{y}(\gamma), \bar{z}(\gamma)]$ by use of an optical filter and an optical sensor in combination.

The spectral sensitivity of this type of photoelectric colorimeter, however, is not entirely identical with the isochromatic function. Consequently, measured values have errors. And also, scattering of the spectral sensitivity among devices such as each optical filter, etc. causes the measured values to have instrumental errors. Therefore, in the case that accuracy of the absolute value as well as a measurement with few instrumental errors is required, a spectral type colorimeter is generally utilized that can bring the spectral sensitivity into a theoretically perfect identity with the isochromatic function. But disadvantageously, this conventional spectral type colorimeter is large-sized and expensive.

SUMMARY OF THE INVENTION

The object of the present invention is, therefore, to provide a tristimulus value type photoelectric colorimeter which has the advantages of being cheap and small-sized, and to minimize such errors in measurement and instrumental errors.

Another object of this invention is to provide a tristimulus value type photoelectric colorimeter in which a recalibration of only one of a plurality of calibration points is required to remove error factors at all channels in measurement such as electrical or mechanical error factors without recalibrating the other calibration points.

The object of this invention is also to provide a tristimulus value type photoelectric colorimeter in which the correction of calibration constants of calibration points is achieved through interpolation using a distance between a chromaticity point of a test piece and each of the calibration points, as a parameter continuously changes a calibration constant of the test piece, so that the test piece can be measured with high accuracy.

In order to achieve the first object, the tristimulus value type photoelectric colorimeter according to the invention is characterized in that it comprises a photoelectric conversion section including an optical filter to analyze light coming from a test piece and reference calibrating samples illuminated with a light source of primary color elements, and a photosensor to convert each of said primary color elements into an electric signal; and a data processing section including a calibration constant calculating means for calculating a calibration constant for each of a plurality of reference calibrating samples on the basis of both information inputted from said photoelectric conversion section and representing the primary color elements of the light coming from each of said reference calibrating samples and a calibration point thereof, a chromaticity point calculation means for calculating a chromaticity point of the test piece and that of each reference calibrating sample in conformity with the information from said photoelectric conversion section, a memory means for memorizing said calibration constant and point of each of the reference calibrating samples and the chromaticity points of the reference calibration point and the chromaticity point of the test piece, a calibration constant selection means for selecting a calibration constant suitable for the test piece from among the calibration constants stored in the memory means in accordance with a distance between the chromaticity point of the test piece and that of each of the reference calibrating samples, and a correction means for correcting measured value which indicates the chromaticity point of the test piece with the calibration constant selected by the calibration constant selection means.

In order to achieve the second object, the tristimulus value type photoelectric colorimeter according to the invention is characterized in that it comprises a photoelectric conversion section including an optical filter to analyze light coming from a test piece and a reference calibrating sample illuminated with a light source of primary color elements, and a photosensor to convert each of said primary color elements into an electric signal; and a data processing section including a calibration constant calculating means for calculating a calibration constant for a reference calibrating sample serving as a criterion on the basis of both information inputted from said photoelectric conversion section and representing primary color elements of the light coming from said reference calibrating sample as a criterion and a calibration point thereof before a calibration constant of each of the other reference calibrating samples is obtained relative to that of the criterion sample on the basis of information representing primary color elements of the light coming from each of the other reference calibrating samples, a calibration point for each of said reference calibrating samples, and the calibration point of said criterion sample, a chromaticity point calculation means for calculating a chromaticity point of the test piece and of each reference calibrating sample, inclusive of the criterion sample, a memory means for memorizing the calibration points and chromaticity points of said reference calibrating samples and the chromaticity point of the test piece, a calibration constant selection means for selecting a calibration constant for the test piece according to a positional relation between the chromaticity point of the test piece and that of each reference calibrating constant which are stored in the memory means, and a correction means for correcting a measured value of the test piece, the correction thereof being carried out with the calibration constant for said criterion sample, which has been calculated by said calibration constant calculating means, in case that only the calibration point of the criterion sample is used for the correction, while, in case that the calibration point of any one of the other reference calibrating samples is used, further calibration constant is estimated from both the calibration constant for the criterion sample and that for each reference calibrating sample stored in the memory means without recalibrating so that the correction of the test piece may be carried out therewith.

In order to achieve the third object, the tristimulus value type photoelectric colorimeter according to the invention is characterized in that it comprises a photoelectric conversion section including an optical filter to analyze light coming from a test piece and a reference calibrating sample illuminated with a light source of primary color elements, and a photosensor to convert each of said primary color elements into an electric signal; and a data processing section including a calibration constant calculating means for calculating a calibration constant for each of a plurality of reference calibrating samples on the basis of both information inputted from said photoelectric conversion section and representing the primary color elements of the light coming from each of said reference calibrating samples and a calibration point thereof, a chromaticity point calculation means for calculating a chromaticity point of the test piece and that of each reference calibrating sample in conformity with the information from said photoelectric conversion section, a memory means for memorizing said calibration constant and calibration point of each of the reference calibrating samples and the chromaticity points of the reference calibration point and the chromaticity point of the test piece, a means for estimating a new calibration constant suitable for the chromaticity point of the test piece between the respective calibration constants of said reference calibrating samples through the interpolation using a positional relation between the chromaticity point of each of said calibration point and that of the test piece as a parameter, and a correction means for correcting measured value of the test piece by the new calibration constant.

BRIEF DESCRIPTION OF THE DRAWINGS

The present invention will now be described with reference to the appended drawings, provided purely by way of non-limiting example, in which.

DETAILED DESCRIPTION OF THE PREFERRED EMBODIMENTS

Figure 1:
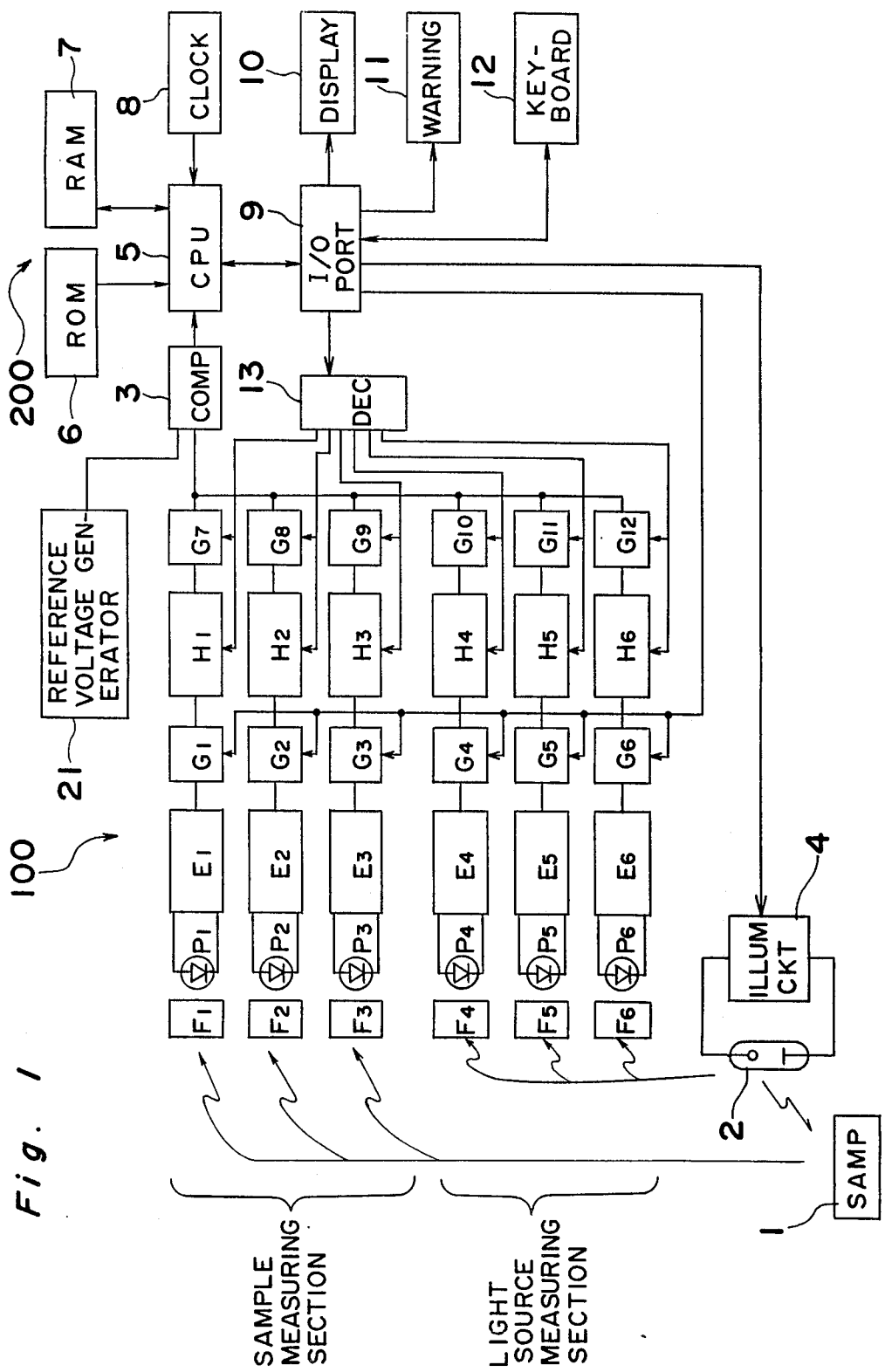
FIG. 1 is a block diagram of an example of the photoelectric colorimeter with spectral sensitivity correcting function according to this invention.
Figure 3:
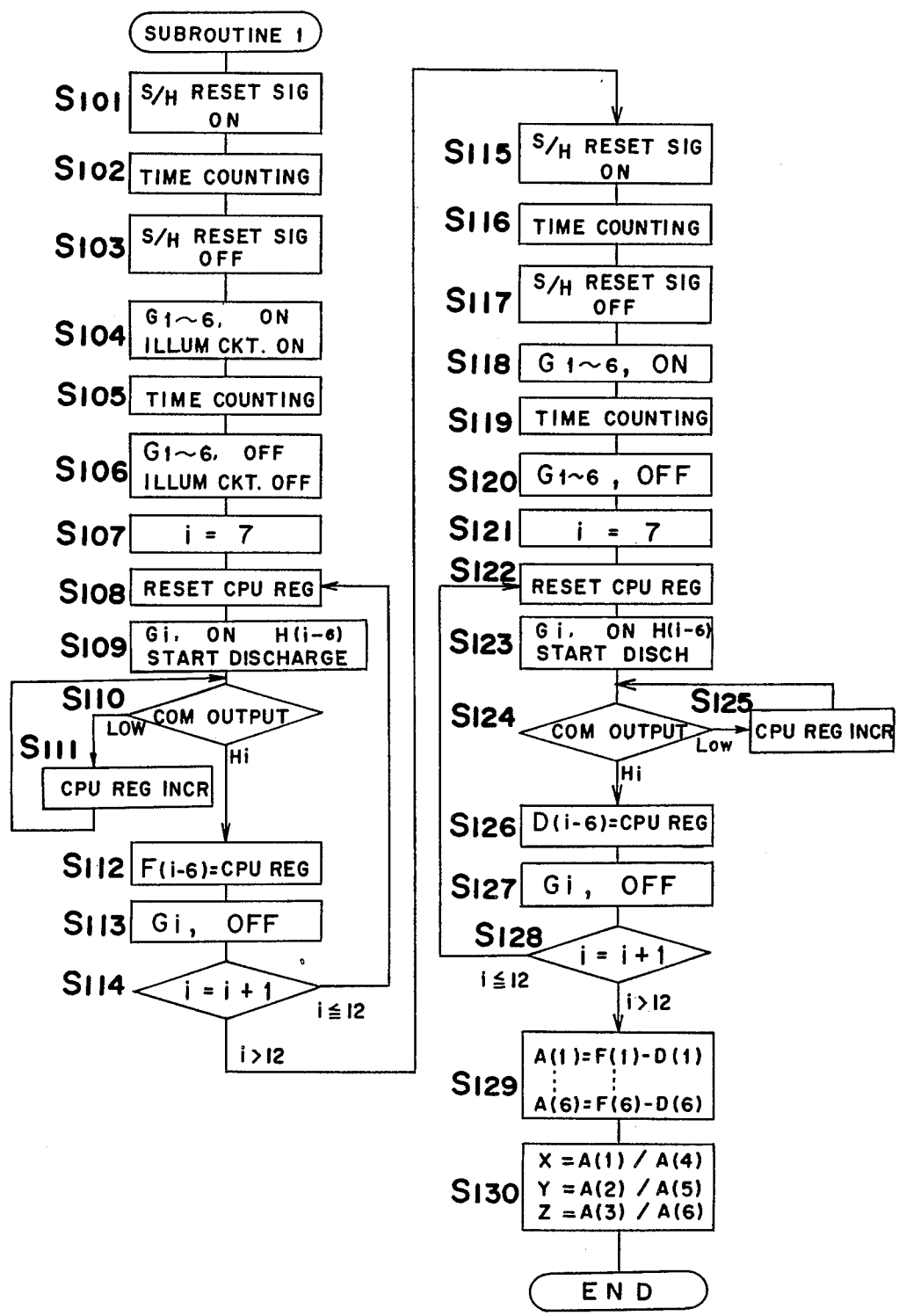
FIG. 3 is a flow chart showing the take-in of the tristimulus value data of the test piece.

Referring now to FIG. 1, the photoelectric colorimeter comprises a photoelectric conversion section 100 and a data processing section 200. The photoelectric conversion section 100 has six photodiodes $P_{1-6}$ of photosensor, of which three photodiodes $P_{1-3}$ are used for measurement of a test piece 1, and remaining three photodiodes $P_{4-6}$ for measurement of a light source 2. Calculating a measured value of the test piece divided by a measured value of the light source cancels fluctuation of the light source 2 and this makes it possible to measure in a constant condition all the time. Light from the test piece 1 or from the light source 2 is analyzed into its primary color elements with optical filters $F_{1-6}$. The color elements analyzed are detected by photodiodes $P_{1-6}$ and converted into electric signals by corresponding photoelectric converter circuits $E_{1-6}$, the electric signals being amplified. Amount of electricity corresponding to the signal representing each of the color elements is stored in each of their corresponding sample-hold circuits $H_{1-6}$ through gates $G_{1-6}$, then transmitted in turn to a comparator 3 through further gates $G_{7-12}$. Central processing unit (CPU) 5, a control section of the data processing section 200, carries out an operation of the tristimulus data (X, Y, Z) on a constant condition where the fluctuation of the light source 2 is canceled, at step $S_{130}$ via steps $S_{101-129}$ as shown in FIG. 3.

At step $S_{101}$, the decoder 13 outputs a reset signal which is controlled by CPU 5 through I/O port 9 signal to sample-hold circuits $H_1$- $H_6$ as shown in FIG. 1. After a predetermined time is counted at step $S_{102}$, the sample-hold reset signal is cleared at step $S_{103}$. Then, at step $S_{104}$, the decoder 13 outputs a signal so as to turn each of gates $G_1$- $G_6$ on and, at the same time, illumination circuit 4 is turned on. Thereafter, at step $S_{105}$, a predetermined time is counted and, then, the program proceeds to step $S_{106}$, at which gates $G_1$- $G_6$ are turned off and at the same time, the illumination circuit 4 is turned off. As a result, each of the sample-hold circuits $H_1$- $H_6$ holds a signal representing the light amount of each of the different primary color elements which has passed through the respective gates $G_1$-$G_6$. Then, at step $S_{107}$, channel selection (i=7) is carried out. Then, at step $S_{108}$, registers of CPU 5 is reset. Thereafter, at step $S_{109}$, gate $G_7$ is turned on and, at the same time, sample-hold circuit $H_1$ starts to discharge electricity. Then, at step $S_{110}$, it is discriminated whether output of the comparator 3 is "Low" or "High". The comparator 3 compares reference voltage outputted from a reference voltage generator 21 with output of the sample-hold circuit $H_1$ and it outputs a signal on "High" level when the output of the latter is lower than the reference voltage. Discrimination of "Low" at step $S_{110}$ applies an increment to a register of CPU 5, that is, value to be stored in the register increases at step S 111. On the other hand, discrimination of "High" brings the program to step $S_{112}$, at which contents of each of the CPU registers are stored in the memory (RAM) 7 as F(1). Thereafter, at step $S_{113}$, gate $G_7$ is turned off. As a result, the analog signal held in the sample-hold circuit $H_1$ is converted into a digital signal F(1) stored in the memory 7. At step $S_{114}$, i+1 is substituted for i and, when $i \leq 12$, the program returns to step $S_{108}$, on the other hand, when $i > 12$, the program proceeds to step $S_{115}$. Thus, in the above procedures, output signals representing informations F(1), F(2), ... F(6) under the condition that the light source is turned on are stored in RAM 7. Steps $S_{115}$ through $S_{128}$ are substantially similar to steps $S_{101}$ through $S_{114}$, except for that measurement is carried out in a state that the light source 2 is off, and output signals representing informations D(1), D(2), ... , D(6) of the photodiodes $P_1$, $P_2$, ..., $P_6$ are calculated. At step $S_{129}$, data D(1), D(2), ..., D(6) are subtracted from data F(1), F(2), ..., F(6) respectively, in order to obtain data A(1), A(2), ..., A(6). This is to remove disadvantages such as an offset of a dark current caused by change with time. Then, at step $S_{130}$, operation of tristimulus values (X, Y, Z) (measured value A(1), A(2), A(3) of the test piece divided by that A(4), A(5), A(6) of the light source, respectively) is carried out so as to cancel fluctuation of the light source 2 and keep constant measuring conditions.

Figure 2:
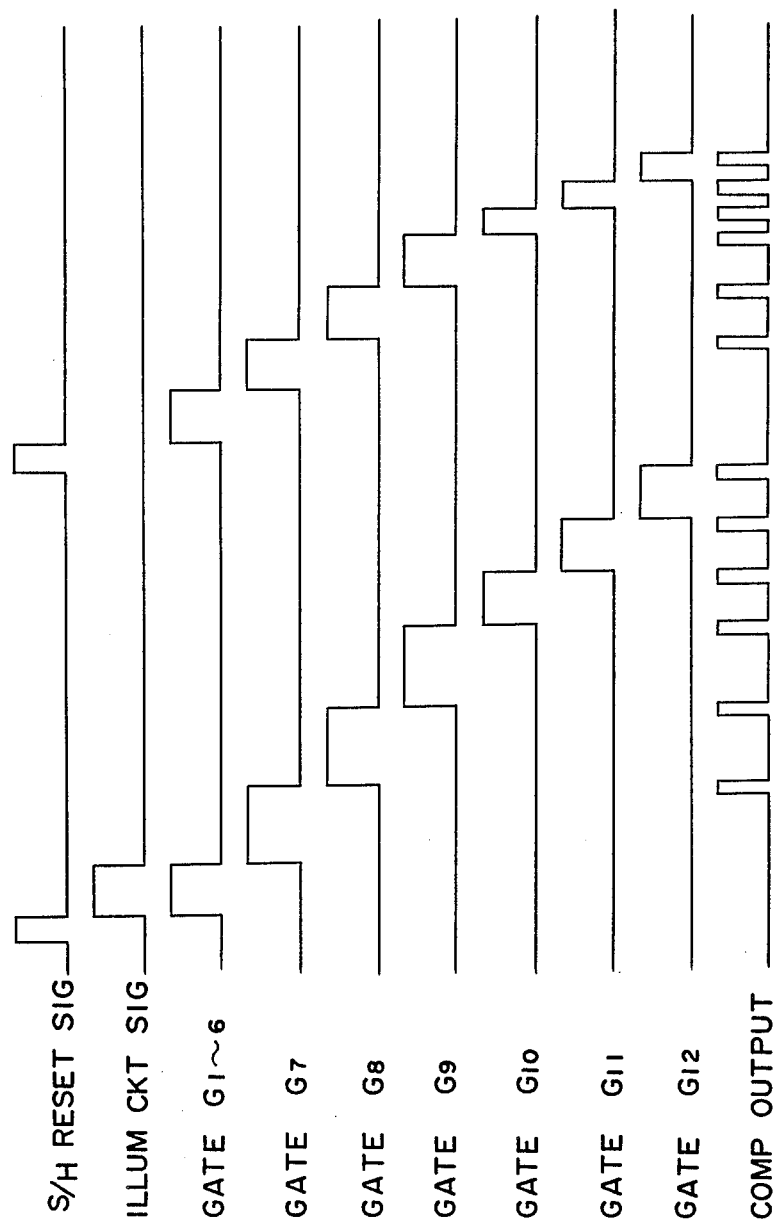
FIG. 2 is a timing chart of the photoelectric conversion section.

In receiving the signal from the photodiodes $P_1$, $P_2$, ..., $P_6$, gates $G_{1-12}$ open with the timing shown in FIG. 2. Output from the comparator 3 is shown in FIG. 2.

The data processing section 200 comprises aforementioned CPU 5 used for controlling and calculation; ROM 6 storing programs for the system controlling, color conversion, etc.; aforementioned RAM 7 as a memory means storing information of color, etc.; a clock 8; an I/O port 9; a display section 10 such as a liquid crystal display device, a printer or the like for displaying results obtained by the measurement, and a keyboard 12 for operating the photoelectric colorimeter. It also comprises a warning section 11 and a decoder 13.

Figure 4:
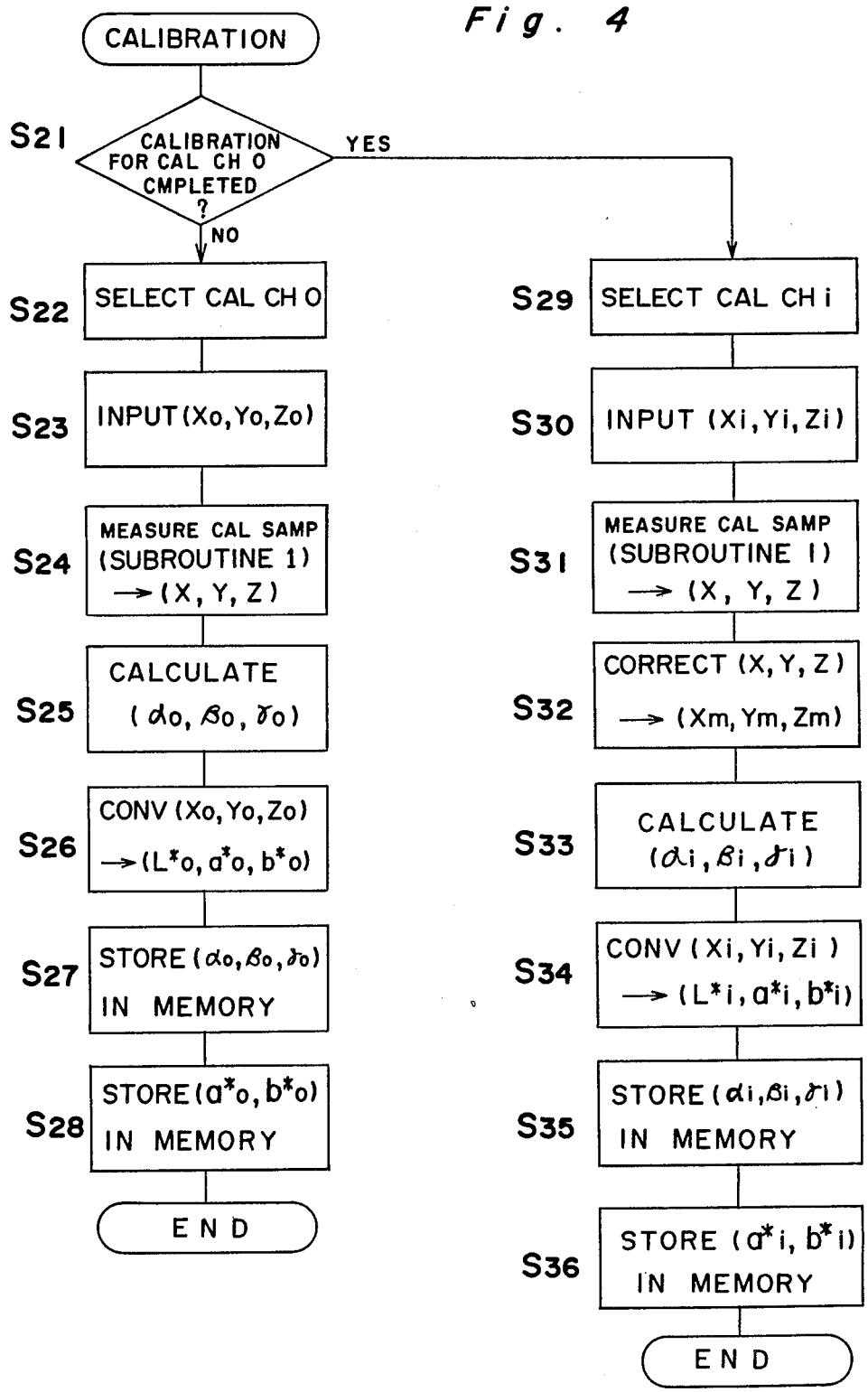
FIG. 4 is a flow chart showing the calculation of the calibration constants and the storage of the chromaticity points of the calibrating reference samples in accordance with a first embodiment.

At the beginning of using the photoelectric colorimeter, it is required to perform a preliminary operation necessary for calibration according to the flow chart shown in FIG. 4. This colorimeter has ten calibrating channels from 0 to 9, and so, the preliminary operation for calibration can be performed with respect to ten kinds of reference calibration samples. This colorimeter requires that the channel 0 should be inputted first. After the calibration with the channel 0, any other channel may be selected as desired. And also, it is possible to remove error factors common to every channel 0, 1, ..., 10 such as temperature, etc. by recalibrating only channel 0, as will be described hereinafter.

A calibrating key on the keyboard 12 is pushed and the colorimeter is brought into a calibrating mode. In step $S_{21}$ it is judged whether or not the calibration has been effected for the channel 0. If not, program proceeds to step $S_{22}$, at which the calibrating channel will automatically come to 0. Then, an operator prepares a reference calibration sample for the calibrating channel 0 and places it at the position of SAMP 1 in FIG. 1. And, at step $S_{23}$ he inputs tristimulus values ($X_0$, $Y_0$, $Z_0$) of the reference calibration samples, that is a calibration point, by means of numerical keys on the keyboard 12. Then, at step $S_{24}$, the reference calibration sample is measured with a measuring key to get tristimulus values (X, Y, Z). At step $S_{25}$, calibration constants ($\alpha_0$, $\beta_0$, $\gamma_0$) are calculated with the following equations.

$$\alpha_0 = \frac{X_0}{X}, \beta_0 = \frac{Y_0}{Y}, \gamma_0 = \frac{Z_0}{Z}$$

At step $S_{26}$, the tristimulus values ($X_0$, $Y_0$, $Z_0$) of the reference calibrating sample are converted into new values ($L_0^*$, $a_0^*$, $b_0^*$) in $L^* a^* b^*$ co-ordinate system so that the conversion of the color space may be effected.

The values obtained are stored in a memory area at steps $S_{27}$ and $S_{28}$ as follows.

$\alpha \text{ memo}(0) = \alpha_0$ $\beta \text{memo}(0) = \beta_0$ $\gamma \text{memo}(0) = \gamma_0$ $a^* \text{memo}(0) = a_0^*$ $b^* \text{memo}(0) = b_0^*$ In $L^* a^* b^*$ co-ordinate system, $L_0^*$ is a luminosity information.

When it is judged that the calibration in the calibrating channel 0 has already been done at step $S_{21}$, any channel can be selected from 1 to 9 arbitrarily at step $S_{29}$. The calibrating channel selected is assumed to be i (i=1–9). The operator prepares a calibration reference sample for calibrating channel i, and subsequently he inputs tristimulus values ($X_i$, $Y_i$, $Z_i$) of the test piece by means of the numerical keys at step $S_{30}$. Then, at step $S_{31}$, the reference calibration sample is measured to obtain tristimulus values (X, Y, Z). Thereafter, at step $S_{32}$, the tristimulus values (X, Y, Z) are corrected using the calibration constants ($\alpha_0$, $\beta_0$, $\gamma_0$) of the calibration channel 0 according to the following equations.

$$Xm = \alpha_0 \cdot X$$

$$Ym = \beta_0 \cdot Y$$

$$Zm = \gamma_0 \cdot Z$$

Calibration constants ($\alpha_i$, $\beta_i$, $\gamma_i$) are calculated by substituting the values obtained (Xm, Ym, Zm) in the following equations.

$$\alpha_i = \frac{X_i}{Xm}, \beta_i = \frac{Y_i}{Ym}, \gamma_i = \frac{Z_i}{Zm}$$

Then, at step $S_{34}$, the tristimulus values ($X_i$, $Y_i$, $Z_i$) of the reference calibrating sample for the channel i are converted relative to the $L^* a^* b^*$ co-ordinate system of different color space. The conversion result ($L_i^*$, $a_i^*$, $b_i^*$) is stored in the memory area.

$$(X_i, Y_i, Z_i) \underset{\text{color conversion}}{\longrightarrow} (L_i^*, a_i^*, b_i^*)$$

At the following step $S_{35}$, the calibration constants ($\alpha_i$, $\beta_i$, $\gamma_i$) are stored in the memory area for calibration constants and subsequently at step $S_{36}$, a chromaticity point ($a_i^*$, $b_i^*$) of the reference calibrating sample is stored in the memory.

$\alpha \text{ memo}(i) = \alpha_i$ $\beta \text{ memo}(i) = \beta_i$ $\gamma \text{ memo}(i) = \gamma_i$ $a^* \text{memo}(i) = a_i^*$ $b^* \text{memo}(i) = b_i^*$ The steps $S_{21}$ through $S_{35}$ shown in FIG. 4 are an example of the calibration constant calculating means.

Figure 5:
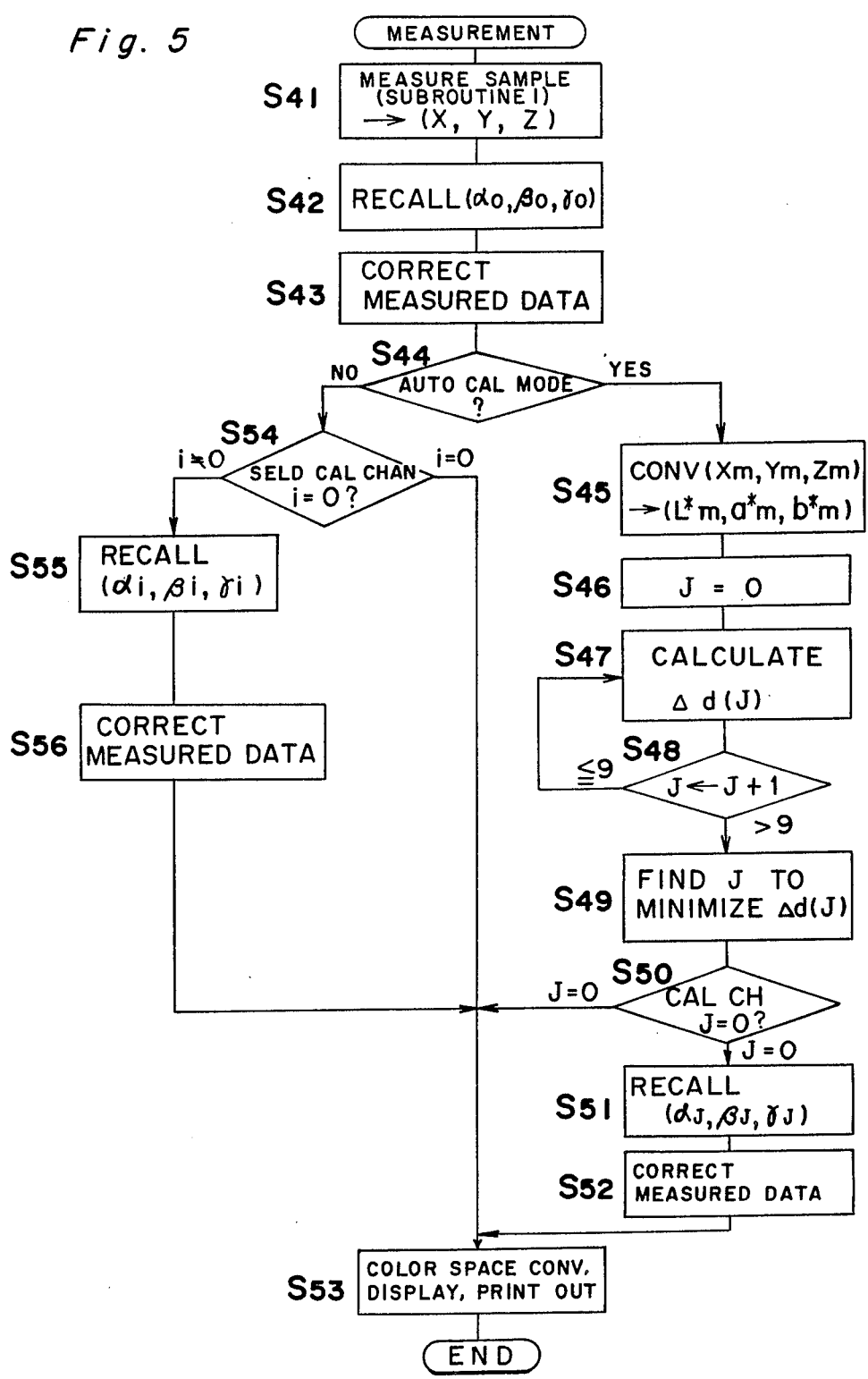
FIG. 5 is a flow chart showing the selection of the calibration constants according to the chromaticity points of the test piece and of the reference calibrating samples and the correction of measured data in accordance with the first embodiment.

Hereinafter, measurement of an actual test piece will be explained according to a flow chart of FIG. 5.

At step $S_{41}$, photometry of the test piece is performed by operating measuring keys to obtain tristimulus values (X, Y, Z) of the test piece. Then, at step $S_{42}$, the calibration data $\alpha_0$, $\beta_0$ and $\gamma_0$ for the calibrating channel 0 are recalled from $\alpha$ memo(0), $\beta$ memo(0) and $\gamma$ memo(0) and at step $S_{43}$, measurement data obtained are corrected with the following equations.

$$Xm = \alpha_0 \cdot X, \quad Ym = \beta_0 \cdot Y, \quad Zm = \gamma_0 \cdot Z$$

Next, at step $S_{44}$, it is judged whether a mode is of automatic calibration or not. Procedures in both cases will be now described.

(I) Case of Automatic Calibration Mode

At step $S_{45}$, the measurement data (Xm, Ym, Zm) of the test piece which have already corrected in the calibrating channel 0 are converted in the L* a* b* co-ordinate system and results obtained are let to be (Lm*, am*, bm*). Subsequently, at steps $S_{47}$ and $S_{48}$ following step $S_{46}$, distances between respective chromaticity points (a*memo(j), b*memo(j)) of the reference calibrating samples for the calibrating channels 0 to 9 and that (am*, bm*) of the test piece are calculated using the following equation.

$$\Delta d(J) = \sqrt{(am^* - a^* \text{ memo } (J))^2 + (bm^* - b^* \text{ memo } (J))^2}$$
$(J = 0\text{-}9)$ At the following step $S_{49}$, from among $\Delta d(0)$ to $\Delta d(9)$ is sought such a J as $\Delta d(J)$ will be minimum. Then, at step $S_{50}$, judgement if J is 0 or not is done. When J is not 0, step $S_{51}$ will follow the previous step, where a calibration constant for the calibrating channel J is recalled from $\alpha$ memo(J), $\beta$ memo(J) and $\gamma$ memo(J). The data of the test piece is corrected in the following equations with the calibration constant $(\alpha_J, \beta_J, \gamma_J)$ for the calibrating channel J at step $S_{52}$, which is followed by Step $S_{53}$.

Xm¢Xm·α memo(J)

Ym¢Ym·β memo(J)

Zm¢Zm·γ memo(J)

When J=0, step $S_{53}$ directly follows step $S_{50}$ because the test piece has already corrected with respect to the channel 0.

At step $S_{53}$, chromatic space conversion into a designated color display system is effected by a color display system switching key, using a tristimulus values (Xm, Ym, Zm), of the test piece, obtained in the above procedure. Results are displayed on the display section (10) and printed out.

As understood from the above description, the absolute measurement errors caused by errors of spectral sensitivity and the instrumental errors caused by the scattering in the spectral sensitivity between instruments are minimized, owing to the fact that a calibration constant of a reference calibrating sample which has a chromaticity point closest to that of the test piece 1 is recalled for correction of the measured values.

(II) Case of Non-automatic Calibration Mode

At step $S_{54}$, a calibrating channel i selected is judged whether i is 0 or not. When the calibrating channel selected is 0, program proceeds to step $S_{53}$. On the other hand, when it is not 0, program proceeds to steps $S_{55}$ and $S_{56}$, where the tristimulus values of the test piece are corrected using the calibration constant of the designated calibrating channel i as follows.

Xm¢Xm·α memo(i)

Ym¢Ym·β memo(i)

Zm¢Zm·γ memo(i)

With the tristimulus values (Xm, Ym, Zm) calculated in the above procedure, color space conversion into the designated color display system is effected by means of the color display system switching key, and then conversion results are displayed on the display section 10 and printed out.

Steps $S_{46}$, $S_{47}$, $S_{48}$ and $S_{49}$ constitute an example of the automatic calibration constant selecting means, while steps $S_{43}$ and $S_{52}$ constitute an example of the correcting means.

As the above example proved, in both cases of automatic and non-automatic calibration modes, correction of the test piece is completed through two steps of correction, that is, correction by the calibration constant for calibration channel 0, and then, correction by the calibration constant for calibration channel i (i≠0) which is beforehand stored in RAM 7. Common error factors in every channel caused by change in optical or electric circuit systems with time are canceled only by recalibration for the channel 0, because the calibration constant for the calibration channel i (i≠0) is represented in the relative form to the calibration constant for the calibration channel 0. Therefore, the recalibration for the calibration channel i (i≠0) is not required.

In the aforementioned embodiment, measured values of the test piece 1 are corrected by the calibration constant of a reference calibrating sample which has a chromaticity point closest to that of the test piece 1. Alternatively, chromaticity area may be divided into a plurality of sections in advance so as to obtain calibration constants with the reference calibrating samples whose respective chromaticity points are in one of the divided sections. Then it may be judged which section contains the chromaticity point of the test piece. Thereby, the measured values may be corrected with the calibration constant in a section where the chromaticity point of the test piece exists. Furthermore, as a second alternative, correction of the measured values may be effected as follows. Several reference calibrating samples each of which has a chromaticity point close to that of the test piece are selected to obtain a new calibration constant with the interpolation method, based on distances between respective chromaticity points of the reference calibrating samples and that of the test piece.

In the embodiment described above, calibration has been effected by an operator with several reference calibrating samples before measurement in the automatic mode is done. But alternatively, a calibration constant for each colorimeter of this invention can be also calculated in its production process and stored in a nonvolatile memory or the like. This enables the colorimeter to measure test pieces with one of various calibration constants stored therein even if an operator does not have a plurality of reference calibrating samples, but has only one reference sample for channel 0. Then, what the operator has to do to use the automatic calibrating mode is only one calibration with the reference calibrating sample for the channel 0.

As is obvious from the above description, the colorimeter according to the invention can minimize the absolute measurement errors caused by spectral sensitivity errors as well as the instrumental errors caused by the scattering in spectral sensitivity between instruments, owing to the fact that calibration constants are calculated with a plurality of reference calibrating samples and stored in the memory, and that an optimum calibration constant is sought from among the calibration constants stored there in accordance with the chromaticity point of the test piece so that the measured values can be corrected.

Now, a second embodiment of the photoelectric colorimeter of the invention will be described. This photoelectric colorimeter is of the same structure in a block diagram as that shown in FIG. 1. FIG. 2 is a timing chart of a photoelectric conversion section 100 of this embodiment. Similarly to the first embodiment, tristimulus values (X, Y, Z) are calculated by CPU 5 at step $S_{130}$ via steps $S_{101-129}$ in FIG. 3 in the constant condition that the fluctuation of the light source 2 is canceled. $F_{(1)}, F_{(2)}, \ldots, F_{(6)}$ at step $S_{112}$ and $D_{(1)}, D_{(2)}, \ldots, D_{(6)}$ at step $S_{126}$ correspond to output of the photodiodes $P_1, P_2, \ldots, P_6$ respectively. In receiving output signals from the photodiodes $P_1, P_2, \ldots, P_6$, the gates $G_{1-12}$ open with the timing shown in FIG. 2.

Figure 6:
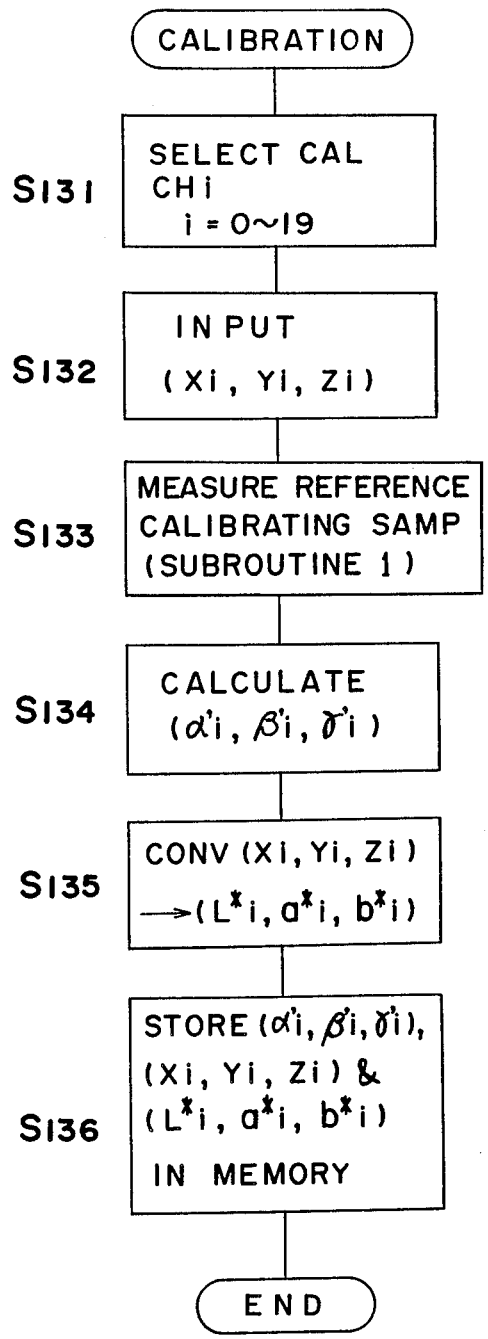
FIG. 6 is a flow chart showing the calculation of the calibration constants, and the storage of the calibration point, calibration constant and chromaticity point of each reference calibrating sample in accordance with a second embodiment.

In using the photoelectric colorimeter, it is required to perform a calibration with a plurality of reference calibrating samples of different colors according to the flow chart shown in FIG. 6. This photoelectric colorimeter has 20 calibrating channels from 0 to 19, and so, calibration can be performed with respect to 20 kinds of reference calibrating samples.

A calibrating key on the keyboard 12 is pushed and the colorimeter is brought into a calibrating mode. At step $S_{131}$, a calibrating channel is selected from among 0 to 19 arbitrarily. A channel selected is assumed to be i (i=0-19). A reference calibrating sample for the calibrating channel i is provided and tristimulus values (Xi, Yi, Zi) which are a calibration point of the reference calibrating sample are inputted with numerical keys at step $S_{132}$. Thereafter, at step $S_{133}$, the reference calibrating sample is measured by means of a measuring key in a subroutine constituted of step $S_{101}$ through $S_{130}$ to obtain tristimulus values (X, Y, Z). Then, at step $S_{134}$, calibration constants (αi', βi', γi') are calculated using the tristimulus values (X, Y, Z) in the following equations.

$$\alpha i' = \frac{Xi}{X}, \beta i' = \frac{Yi}{Y}, \gamma i' = \frac{Zi}{Z}$$

wherein $$\alpha_0' = \alpha_0, \quad \beta_0' = \beta_0, \quad \gamma_0' = \gamma_0$$
$$\alpha i' = \alpha_0 \cdot \alpha i, \quad \beta i' = \beta_0 \cdot \beta i, \quad \gamma i' = \gamma_0 \cdot \gamma i$$
$(i \neq 0)$ At step $S_{135}$, the tristimulus values (Xi, Yi, Zi) of the reference calibrating sample are transformed to the L*i, a*i, b*i co-ordinate system of different color system. Results obtained by the color space transformation are assumed to be (L*i, a*i, b*i)

$$(Xi, Yi, Zi) \rightarrow (L*i, a*i, b*i)$$
color space transformation where L*i is a luminosity information.

Next, at step $S_{136}$, the calibration constants obtained (αi', βi', γi'), the calibration point (Xi, Yi, Zi) and the chromaticity point (L*i, a*i, b*i) of the reference calibrating sample i are stored in a memory area.

Figure 7:
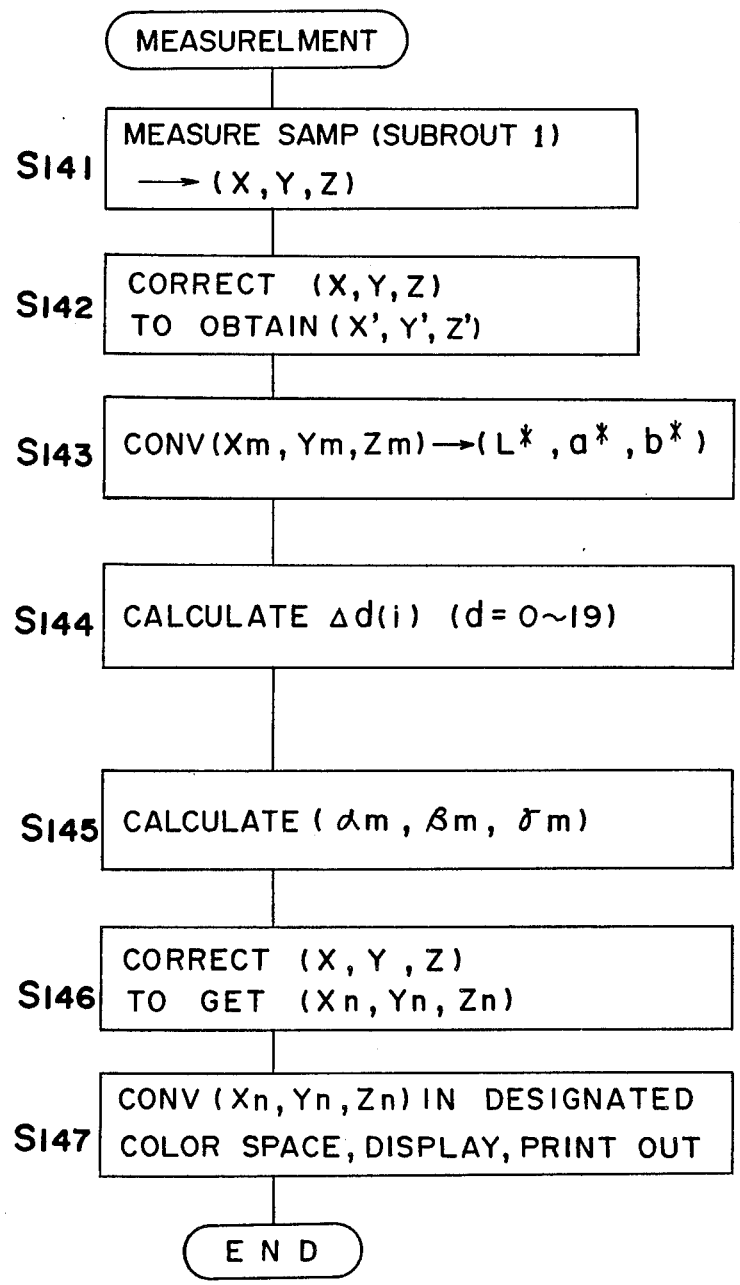
FIG. 7 is a flow chart showing calculation of the calibration constant suitable for the test piece through the interpolation between the chromaticity points of the reference calibrating samples in accordance with the second embodiment.

Now, measurement of an actual test piece will be described according to the flow chart shown in FIG. 7.

First, at step $S_{141}$, a test piece 1 to be measured is measured with a measuring key in the subroutine constituted of steps $S_{101}$ through $S_{130}$ to obtain tristimulus values (X, Y, z) of the test piece 1. At step $S_{142}$, calibration constants (α0', β0', γ0') for the calibrating channel 0 are recalled. Correction of the measurement data (X, Y, Z) using the following equations provides new tristimulus values (Xm, Ym, Zm).

$$Xm = \alpha_0' \cdot X, \quad Ym = \beta_0' \cdot Y, \quad Zm = \gamma_0' \cdot Z$$

Then, at step $S_{143}$, the tristimulus values (Xm, Ym, Zm) calculated at the previous step $S_{142}$ are converted into new values (L*m, a*m, b*m) in the L* a* b* co-ordinate system of different color space.

$$(Xm, Ym, Zm) \rightarrow (L*m, a*m, b*m)$$
color space conversion

At step $S_{144}$, distance Δd(i) between a chromaticity point (a*m, b*m), of the test piece, obtained as a result of the correction with respect to the calibrating channel 0 and that (a*i, b*i) (i=0-19) of the calibration point of each reference calibrating sample for the calibrating channels 0-19 is calculated according to the following equation.

$$\Delta d(i) = \sqrt{(a*m - a*i)^2 + (b*m - b*i)^2}$$
$(i = 0-19)$

At step $S_{145}$, calculation of the following operation expresion (1) is carried out using the distance Δd(i) as a parameter so as to obtain optimum calibration constants (αm, βm, γm) suitable for the chromaticity point (a*m, b*m) of the test piece.

OPERATION EXPRESSION (1)

$$k_0 = \left(\frac{1}{\Delta d(0)}\right)^n, k_1 = \left(\frac{1}{\Delta d(1)}\right)^n, \ldots, k_{19} = \left(\frac{1}{\Delta d(19)}\right)^n$$

where Δd≠0, and n is a constant.

$$k = k_0 + k_1 + \ldots + k_{19}$$

$$K_0 = \frac{k_0}{k}, K_1 = \frac{k_1}{k}, \ldots, K_{19} = \frac{k_{19}}{k}$$

$$\begin{cases} \alpha_m = K_0 \cdot \alpha_0' + K_1 \cdot \alpha_1' + \ldots + K_{19} \cdot \alpha_{19}' \\ \beta_m = K_0 \cdot \beta_0' + K_1 \cdot \beta_1' + \ldots + K_{19} \cdot \beta_{19}' \\ \gamma_m = K_0 \cdot \gamma_0' + K_1 \cdot \gamma_1' + \ldots + K_{19} \cdot \gamma_{19}' \end{cases}$$

Then, at step $S_{146}$, the tristimulus values (X, Y, Z), obtained at step $S_{141}$, of the test piece are calibrated using the following equation so as to obtain tristimulus values (Xn, Yn, Zn).

$$X_n = \alpha_m \cdot X, \quad Y_n = \beta_m \cdot Y, \quad Z_n = \gamma_m \cdot Z$$

Finally, at step $S_{147}$, color space conversion into a designated color display system is performed by a color display system switching key on the keyboard 12, and then, conversion results are displayed on the display section 10 and printed out.

As is obvious in the above description on the second embodiment, 20 calibrating channels i (i=0–19) are provided so as to calculate calibration constants ($\alpha i'$, $\beta i'$, $\gamma i'$) of each of 20 kinds of reference calibration samples. After that, the calibration constant for the test piece to be measured is corrected through interpolation which is performed by calculating an operation expression using as a parameter a relation in position between the test piece and each of the reference calibrating samples which relation is indicated by distance $\Delta d(i)$ between the chromaticity points of the both, so that new calibration constants ($\alpha m$, $\beta m$, $\gamma m$) are obtained. Accordingly, calibration constants for the test piece can be continuously changed to provide each of measured data of the test piece with optimum calibration constants ($\alpha m$, $\beta m$, $\gamma m$) for correction, so that continuity of measured data of the test piece and a high accuracy of measurement are achieved.

Figure 8:
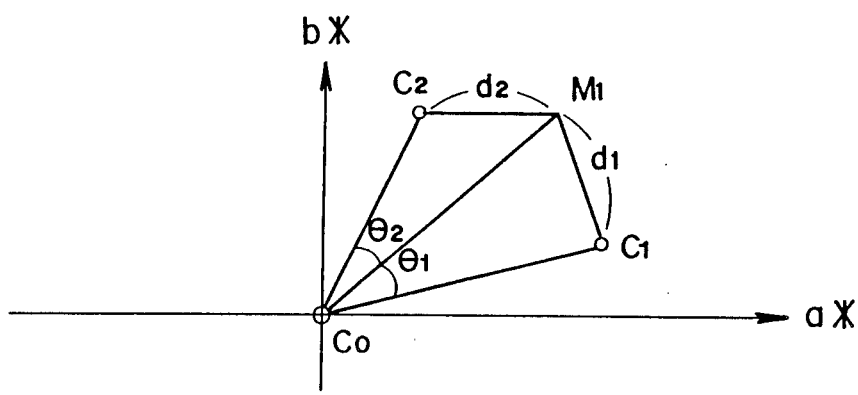
FIG. 8 is an illustration showing a distance and a hue angle between chromaticity points in accordance with the second embodiment.

Operation expression (1), in which only distance $\Delta d(i)$ between a chromaticity point of the test piece 1 and that of each of the calibrating samples is used as a parameter to make correction of the calibration constants in each of the calibration points, is used in the above embodiment. Besides, the following operation expression (2) may be used, in which difference in hue between the chromaticity of the test piece and that of each of the calibration points is added as another parameter (See FIG. 8, where $C_0$, $C_1$, $C_2$: chromaticity points for calibration channels 0–2; $M_1$: chromaticity point of the test piece; $\theta_1$, $\theta_2$: difference in hue angle between the chromaticity point of the test piece and that of each calibration channel; $d_1$, $d_2$: distance between the chromaticity point of the test piece and that of each calibration channel; n, n': constants).

OPERATION EXPRESSION (2)

$$k_0 = \left(\cos\frac{\theta_0}{2}\right)^n \cdot \left(\frac{1}{e^{\Delta d(0)}}\right)^{n'}$$

$$k_1 = \left(\cos\frac{\theta_1}{2}\right)^n \cdot \left(\frac{1}{e^{\Delta d(1)}}\right)^{n'}$$

$$\vdots$$

$$k_0 = \left(\cos\frac{\theta_{19}}{2}\right)^n \cdot \left(\frac{1}{e^{\Delta d(19)}}\right)^{n'}$$

$$k = k_0 + k_1 + \ldots + k_{19}$$

$$K_0 = \frac{k_0}{k}, \quad K_1 = \frac{k_1}{k}, \quad \ldots, \quad K_{19} = \frac{k_{19}}{k}$$

$$\begin{cases} \alpha_m = K_0 \cdot \alpha_0' + K_1 \cdot \alpha_1' + \ldots + K_{19} \cdot \alpha_{19}' \\ \beta_m = K_0 \cdot \beta_0' + K_1 \cdot \beta_1' + \ldots + K_{19} \cdot \beta_{19}' \\ \gamma_m = K_0 \cdot \gamma_0' + K_1 \cdot \gamma_1' + \ldots + K_{19} \cdot \gamma_{19}' \end{cases}$$

There may be further operation expressions for interpolation, one of which, for example, may have two kinds of parameters made by analyzing distance $\Delta d(i)$ into a* co-ordinate element and b* co-ordinate element. Three L*, a* and b* co-ordinate elements of the distance $\Delta d(i)$ may be parameters.

Figure 9:
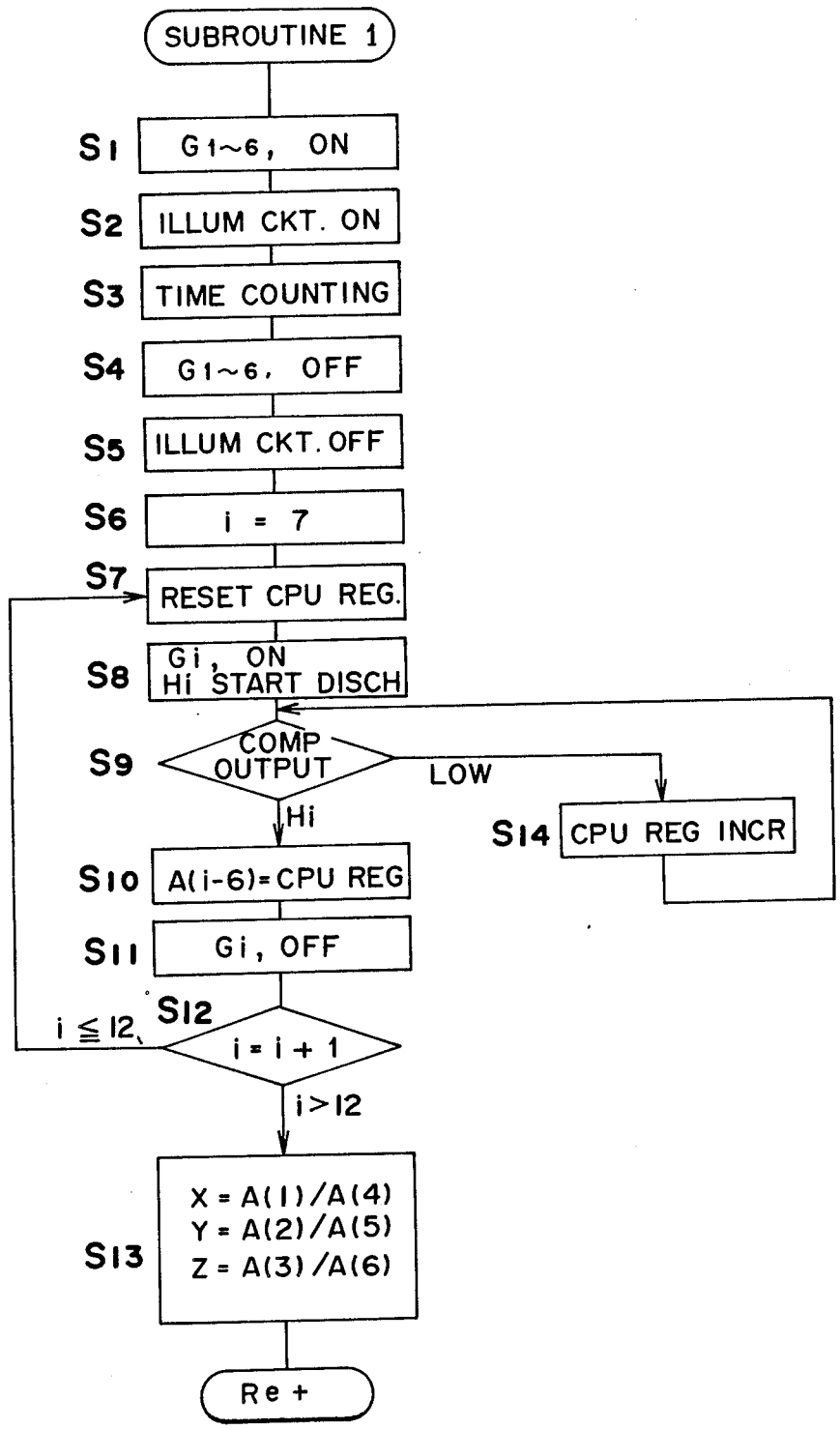
FIG. 9 is a flow chart of the photoelectric conversion section which is a simplified modification from FIG. 3.
Figure 10:
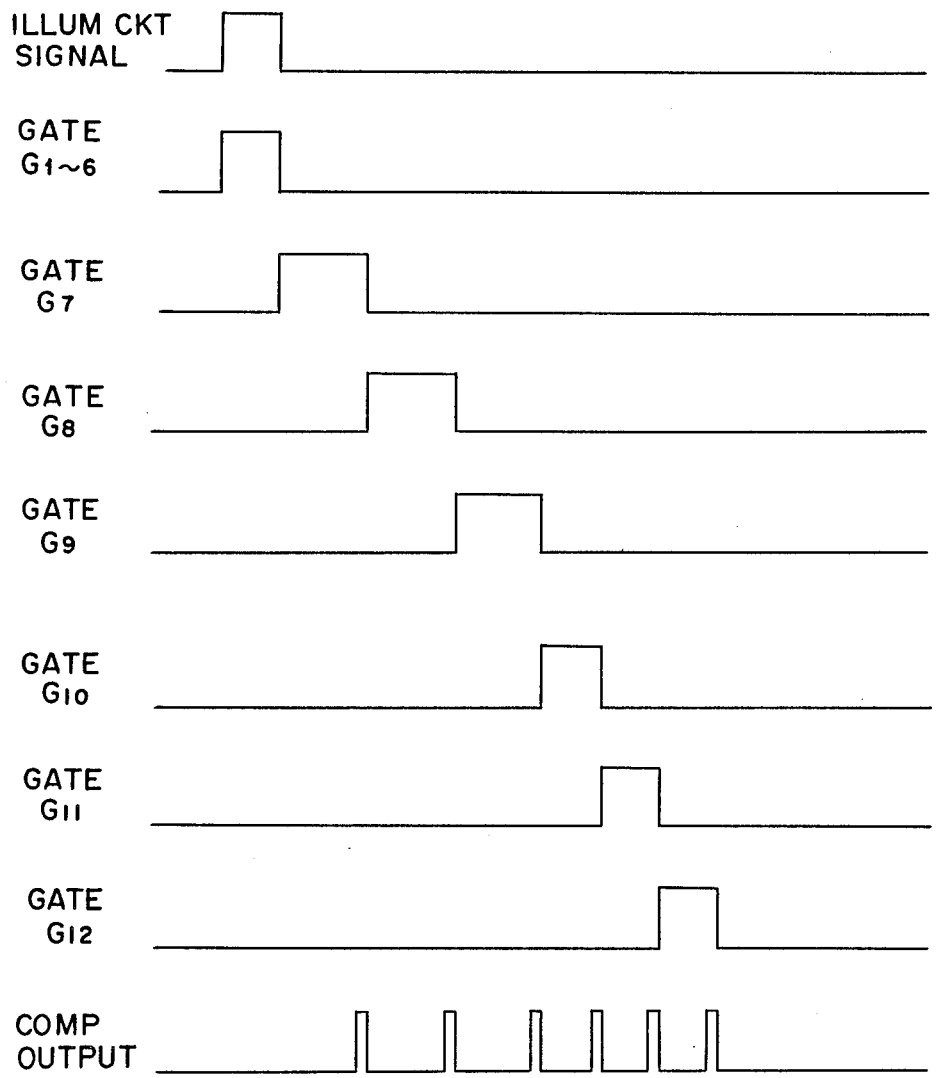
FIG. 10 is a timing chart of the simplified modification in FIG. 9.

FIG. 9 corresponds to a simplified flow of steps $S_{101}$ through $S_{130}$ in FIG. 3, with steps $S_{115}$ to $S_{129}$ omitted by treating F(i-6) as A(i-6). This simplification is possible if the influence of dark current is negligible. FIG. 10 is a wave chart showing a timing of opening and closing of each of gates $G_1$ through $G_{12}$, output of the comparator 3 and output of the illumination circuit 4, in a flow chart of FIG. 10.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A photoelectric colorimeter which comprises:
   a photoelectric conversion section including a spectral separating element to analyze light coming from a test sample and a reference calibrating samples illuminated with a light source into primary color elements, and a photosensor to convert each of said primary color elements into an electric signal; and
   a data processing section including a calibration constant calculating means for calculating a calibration constant for each of a plurality of reference calibrating samples on the basis of both information inputted from said photoelectric conversion section and representing the primary color elements of the light coming from each of said reference calibrating samples and a calibration point thereof, a chromaticity point calculation means for calculating a chromaticity point of the test sample and that of each reference calibrating sample in conformity with the information from said photoelectric conversion section, a memory means for memorizing said calibration constant and point of each of the reference calibrating samples, the chromaticity points of the reference calibration points and the chromaticity point of the test sample, a calibration constant selection means for selecting a calibration constant suitable for the test sample from among the calibration constants stored in the memory means in accordance with a distance between the chromaticity point of the test sample and that of each of the reference calibrating samples, and a correction means for correcting measured value which indicates the chromaticity point of the test sample with the calibration constant selected by the calibration constant selection means.

2. A photoelectric colorimeter which comprises:
   a photoelectric conversion section including an optical filter to analyze light coming from a test sample and a reference calibrating sample illuminated with a light source into primary color elements, and a photosensor to convert each of said primary color elements into an electric signal; and
   a data processing section including a calibration constant calculating means for calculating a calibration constant for a reference calibrating sample serving as a criterion on the basis of both information inputted from said photoelectric conversion section and representing primary color elements of the light coming from said reference calibrating sample as a criterion and a calibration point thereof before a calibration constant of each of the other reference calibrating samples is obtained relative to that of the criterion sample on the basis of information representing primary color elements of the light coming from each of the other reference calibrating samples, a calibration point for each of said reference calibrating samples, and the calibration point of said criterion sample, a chromaticity point calculation means for calculating a chromaticity point of the test sample and of each reference calibrating sample, inclusive of the criterion sample, a memory means for memorizing the calibration points and chromaticity points of said reference calibrating samples and the chromaticity point of the test sample, a calibration constant selection means for selecting a calibration constant for the test sample according to a positional relation between the chromaticity point of the test sample and that of each reference calibrating constant which are stored in the memory means, and a correction means for correcting a measured value of the test sample, the correction thereof being carried out with the calibration constant for said criterion sample, which has been calculated by said calibration constant calculating means, in case that only the calibration point of the criterion sample is used for the correction, while, in case that the calibration point of any one of the other reference calibrating samples is used, further calibration constant is estimated from both the calibration constant for the criterion sample and that for each reference calibrating sample stored in the memory means without recalibrating so that the correction of the test sample may be carried out therewith.

3. A photoelectric colorimeter which comprises:
a photoelectric conversion section including a spectral separating element to analyze light coming from a test sample and a reference calibrating sample illuminated with a light source into primary color elements, and a photosensor to convert each of said primary color elements into an electric signal; and
a data processing section including a calibration constant calculating means for calculating a calibration constant for each of a plurality of reference calibrating samples on the basis of both information inputted from said photoelectric conversion section and representing the primary color elements of the light coming from each of said reference calibrating samples and a calibration point thereof, a chromaticity point calculation means for calculating a chromaticity point of the test sample and that of each reference calibrating sample in conformity with the information from said photoelectric conversion section, a memory means for memorizing said calibration constant and calibration point of each of the reference calibrating samples, the chromaticity points of the reference calibration points and the chromaticity point of the test sample, a means for estimating a new calibration constant suitable for the chromaticity point of the test sample between the respective calibration constants of said reference calibrating samples through the interpolation using a positional relation between the chromaticity point of each of said calibration point and that of the test sample as a parameter, and a correction means for correcting measured value of the test sample by the new calibration constant.

4. A photoelectric colorimeter of tristimulus value type comprising:
means for providing a source light;
a plurality of light receiving means for receiving light coming from a test sample and a plurality of reference calibrating samples illuminated with the source light to produce a plurality of output signals, each of said plurality of light receiving means having a spectral sensitivity different from that of the others;
means for storing a plurality of kinds of calibration constants, each of which corresponds to each of the spectral sensitivites of the plurality of light receiving means, respectively, to produce a plurality of calibration constant signals corresponding to the stored plurality of kinds of calibration constants;
means for calculating a tristimulus value in accordance weith the plurality of output signals of the plurality of light receiving means to produce a tristimulus value signal corresponding to the calculated tristimulus value;
means for automatically determining a final calibration constant in accordance with the plurality of calibration constant signals and the plurality of output signals of the plurality of light receiving means, and
means for calibrating the calculated tristimulus value with the final calibration constant to produce a final tristimulus value signal corresponding to the calbrated tristimulus value.

5. A photoelectric colorimeter according to claim 4, wherein said determining means includes means for selecting optimum one from the plurality of kinds of calibration constants in said storing means.

6. A photoelectric colorimeter according to claim 5, wherein said selecting means includes means for automatically pick up the optimum one of the calibration constants in response to said generating means.

7. A photoelectric colorimeter according to claim 4, wherein said determining means includes means for automatically carrying out the final calibration constant determination in response to said generating means.

8. A photoelectric colorimeter according to claim 7, wherein said automatically carrying-out means includes means for determining the final calibration constant by means of the interpolation with the calibration constants in said storing means.

9. A photoelectric colorimeter according to claim 4, further comprising means for obtaining the calibrating constant in accordance with said receiving means for the storage by said storing means.

10. A photoelectric colorimeter according to claim 4, wherein said storing means includes storage of a standard calibration constant and other calibration constants modified with the standard calibration constant, and wherein said calibrating means is always responsive to the standard calibration constant in addition to the final calibration constant.

11. A photoelectric colorimeter of tristimulus value type comprising:
means for providing a source light;
a plurality of light receiving means for receiving light coming from a test sample and a plurality of reference calibrating samples illuminated with the source light to produce a plurality of output signals, each of said plurality of light receiving means having a spectral sensitivity different from that of the others;

means for storing a plurality of kinds of calibration constants, each of which corresponds to each of the spectral sensitivities of the plurality of light receiving means, respectively, said storing means including storage of a standard calibration constant and other calibration constant modified with the standard calibration constant, to produce a plurality of calibration constant signals corresponding to the stored plurality of kinds of calibration constants;

means for calculating a tristimulus value in accordance with the plurality of output signals of the plurality of light receiving means to produce a tristimulus value signal corresponding to the calculated tristimulus value;

means for automatically determining a final calibration constant in accordance with the plurality of calibration constant signals and the plurality of output signals of the plurality of light receiving means, and means for calibrating the calculated tristimulus value with the final calibration constant to produce a final tristimulus value signal corresponding to the calibrated tristimulus value, said calibrating means being always responsive to the standard calibration constant in addition to the final calibration constant.

12. A photoelectric colorimeter of tristimulus value type comprising:

means for providing a source light;

a plurality of light receiving means for receiving the source light by way of an object and producing corresponding signal characteristics of the object, each of said plurality of light receiving means having a spectral sensitivity different from that of the others;

means for calculating a tristimulus value of the object in accordance with the corresponding signals;

first means for providing a first standard calibration constant;

second means for providing a plurality of kinds of second calibration constants required for correcting a variety of tristimulus values corresponding to different colors, each of the plurality of kinds of second calibration constants corresponding respectively to each of the spectral sensitivities of the plurality of light receiving means;

means for selecting one of the second calibration constants in accordance with the corresponding signals;

means for modifying the selected second calibration constants with the first standard calibration constant to determine a final calibration constant, and means for calibrating the calculated tristimulus value with the final calibration constant to produce a final tristimulus value signal corresponding to the calibrated tristimulus value.

13. A photoelectric colorimeter according to claim 12, wherein said selecting means includes means for selecting an optimum calibration constant from the plurality of second calibration constants.

14. A photoelectric colorimeter according to claim 12, further comprising means for obtaining the first standard calibration constant and the plurality of second calibration constants in accordance with said light receiving means for storage.

15. A photoelectric colorimeter according to claim 12, wherein said modifying means includes means for automatically carrying out the final calibration constant determination in response to the calculated tristimulus value.

16. A photoelectric colorimeter according to claim 13, wherein said selecting means includes means for automatically selecting the optimum calibration constant in response to the calculated tristimulus value.

17. A photoelectric colorimeter according to claim 15, wherein said automatically carrying out means includes means for determining the final calibration constant by means of interpolation of the calibration constants.

* * * * *